(12) United States Patent
Roussel-Maupetit et al.

(10) Patent No.: US 9,782,352 B2
(45) Date of Patent: *Oct. 10, 2017

(54) PHARMACEUTICAL COMPOSITION COMPRISING KREBS CYCLE PRECURSOR SALT, IN PARTICULAR CITRATE SALT, AND USE THEREOF AS A MEDICAMENT

(75) Inventors: Caroline Roussel-Maupetit, Saint-Ismier (FR); Luc-Andre Granier, Montfrin (FR); Catherine Guittet, Arles (FR)

(73) Assignee: ADVICENNE, Nimes (FR)

( * ) Notice: Subject to any disclaimer, the term of this patent is extended or adjusted under 35 U.S.C. 154(b) by 314 days.

This patent is subject to a terminal disclaimer.

(21) Appl. No.: 13/884,062

(22) PCT Filed: Nov. 18, 2011

(86) PCT No.: PCT/FR2011/052691
§ 371 (c)(1),
(2), (4) Date: May 8, 2013

(87) PCT Pub. No.: WO2012/066254
PCT Pub. Date: May 24, 2012

(65) Prior Publication Data
US 2013/0224297 A1 Aug. 29, 2013

(30) Foreign Application Priority Data
Nov. 18, 2010 (FR) ..................... 10 59468

(51) Int. Cl.
*A61K 9/28* (2006.01)
*A61K 31/194* (2006.01)
*A61K 31/16* (2006.01)

(52) U.S. Cl.
CPC .............. *A61K 9/28* (2013.01); *A61K 9/2866* (2013.01); *A61K 31/16* (2013.01); *A61K 31/194* (2013.01)

(58) Field of Classification Search
CPC ...... A61K 9/28; A61K 31/194; A61K 9/2866; A61K 31/16
See application file for complete search history.

(56) References Cited

U.S. PATENT DOCUMENTS

| | | | |
|---|---|---|---|
| 7,645,459 B2 | 1/2010 | Dansereau et al. | |
| 2003/0129228 A1 | 7/2003 | Kay et al. | |
| 2005/0260262 A1 | 11/2005 | Dansereau et al. | |
| 2008/0081068 A1* | 4/2008 | Oberegger ........... | A61K 9/2027 424/465 |
| 2008/0131504 A1 | 6/2008 | Walsdorf, Sr. et al. | |
| 2009/0028935 A1 | 1/2009 | Arnold et al. | |
| 2010/0221335 A1 | 9/2010 | Kanamaru et al. | |

FOREIGN PATENT DOCUMENTS

| | | | |
|---|---|---|---|
| DE | 22 52 665 A | | 5/1973 |
| EP | 0 429 157 A2 | | 5/1991 |
| EP | 1 970 066 | * | 9/2008 |
| GB | 1403900 | | 8/1975 |
| JP | 61-53214 | | 3/1986 |
| JP | 64-16 | | 1/1989 |
| JP | 2008-535912 | | 9/2008 |
| WO | 97/02017 A1 | | 1/1997 |
| WO | 2009-028598 | | 3/2009 |

OTHER PUBLICATIONS

Goldfarb ("Urinary Alkalization," Cystinuria Support Network Internet Article, Sep. 27, 2008).*
Harvey et al. (J Clin Pharmacol 1989;29:338-341).*
K-Lyte, Feb. 6, 2014.*
Goldfarb ("Urinary Alkalization," Cystinuria Support Network Internet Article, Sep. 27, 2008.*
Hess, B., "Erreurs pathophysiologiques, Investigations simples/extensives, roles de l'alimentation, medicaments et pathologie lithiasique renale—ou se situe l'evidence?", Forum Med. Suisse, No. 45, Nov. 7, 2001, pp. 1119-1127.
Wolffram et al., "Transport of Tri- and Dicarboxylic Acids Across the Intestinal Brush Border Membrane of Calves", American Institute of Nutrition, Sep. 18, 1989, pp. 767-774.
Harvey et al., "Bioavailability of citrate from two different preparations of potassium citrate", The Journal of Clinical Pharmacology, 1989, vol. 29, pp. 338-341.
JP Office Action, dated Jul. 7, 2015; Application No. 2013-539316. Pharmaceutical products interview form, "Tablet formulated Uralyt," Sep. 2010.
Biyani C S et al.: "Cystinuria—Diagnosis and Management", EAU—EBU Update Series, Elsevier, Amsterdam, NL, vol. 4. No. 5. Oct. 1, 2006 (Oct. 1, 2006) • pp. 175-183, XP024992348, ISSN: 1871-2592, DOI:DOI;I0.I016/J.EEUS.2006.06.001 [retrieved on Oct. 1, 2006] abstract p. 178. col. 2, line 29—p. 170. col. 1, line 7, Cited in ISR.
"Urocit—K Highlights of Prescribing Information" fda Website, Dec. 31, 2009 (Dec. 31, 2009), pp. 1-4, XP055002516, Retrieved from the Internet: URL:http://www.accessdata.fda.gov/drugsatf da docs/abel/2010/019071s012IbI.pdf [retrieved on Jul. 11, 2011] the whole document, Cited in ISR.
International Search Report, dated Jan. 25, 2012, from corresponding PCT application.

* cited by examiner

*Primary Examiner* — Snigdha Maewall
(74) *Attorney, Agent, or Firm* — Browdy and Neimark, PLLC

(57) ABSTRACT

A solid oral pharmaceutical composition in the form of a tablet consisting of a core including a Krebs cycle precursor salt as active ingredient, and of a coating including a coating agent, the composition including from 40% to 80% by weight of this precursor salt on the basis of the total weight of the composition, the composition being able to release this salt in vitro, both in purified water at pH 7 and in a solution buffered at pH 1.3, with a dissolution device in accordance with the European Pharmacopoeia, at a rate of from 2 to 15% in 15 minutes, from 15 to 25% in 30 minutes, and from 30 to 50% in one hour. The composition is a usefeul medicament, in particular in the treatment and/or prevention of urinary lithiasis occurring at a physiological pH and/or during urinary acidosis and/or during hypocitraturia and/or during hypercalciuria and/or during hyperoxaluria.

10 Claims, 1 Drawing Sheet

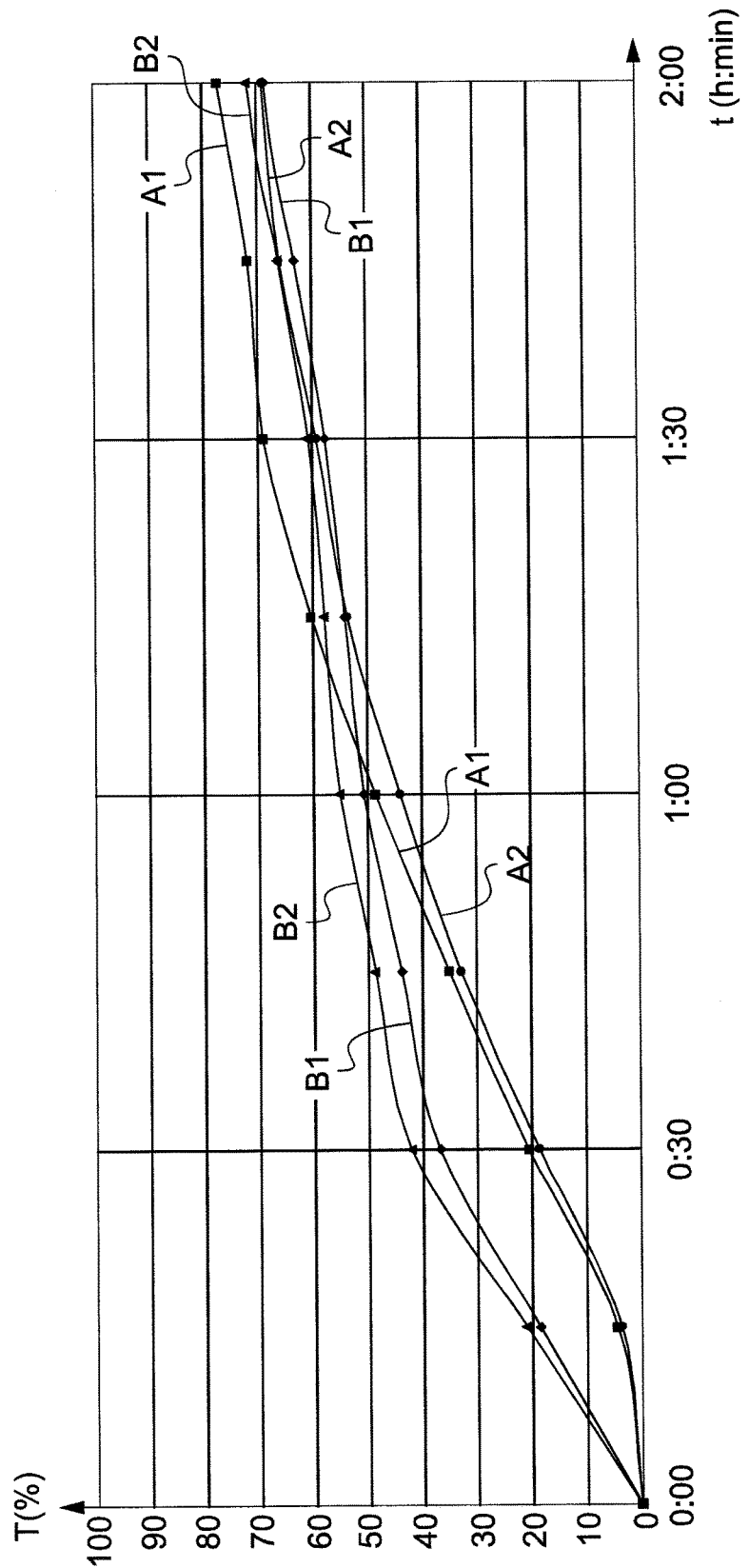

PHARMACEUTICAL COMPOSITION COMPRISING KREBS CYCLE PRECURSOR SALT, IN PARTICULAR CITRATE SALT, AND USE THEREOF AS A MEDICAMENT

The present application relates to a pharmaceutical composition comprising at least one Krebs cycle precursor salt, in particular a citrate salt, used in particular for the treatment and/or prevention of urinary lithiases occurring at a physiological pH and/or during urinary acidosis and/or during hypocitraturia and/or during hypercalciuria and/or during hyperoxaluria.

The physiological urinary pH is typically of the order of about 5 to 5.5.

Urinary acidosis and/or hypocitraturia and/or hypercalciuria and/or hyperoxaluria are generally indications of urinary lithiasis.

Urinary lithiasis is a disease consisting of the formation of calculi in the urinary tract. A urinary calculus consists mainly of crystalline substances. Crystallization is closely related to saturation of the urine with crystallizable compounds such as calcium, oxalate, phosphorus, magnesium, bicarbonate, uric acid, urate, sodium or cystine. These various compounds eliminated in the urine are therefore directly involved, through their concentration and their tendency to crystallize, in the formation of calculi. However, this tendency is also influenced by various crystallization inhibiting or inducing substances. Thus, the Krebs cycle precursor salts, and in particular the citrate ion, have an inhibitory action on the formation of certain calculi, limiting or even preventing crystal growth, aggregation and nucleation in vivo and in vitro.

One treatment for urinary lithiasis is alkalization of the urine. Alkaline compositions comprising alkaline salts are generally indicated in the treatment of urinary acidosis and/or hypocitraturia and/or hypercalciuria and/or hyperoxaluria, but also of certain tubulopathies including cystinuria, as well as certain hereditary metabolic diseases.

Among the alkaline salts used, the citrate salt and more particularly potassium citrate may be mentioned.

One of the advantages of the citrate salts is that they are excreted by the kidneys. Urinary citrate results from this renal tubular excretion, as well as, possibly, from direct urinary elimination of an excessive exogenous supply, leading to alkalization of the urine. Another advantage of citrate is that it complexes with calcium in the urine. Thus, it is one of the ions most used for preventing the formation of calculi from calcium phosphate, calcium oxalate, uric acid and cystine, owing to its capacity for alkalizing the urine and for eliminating supersaturation of the urine with calcium oxalate ions.

Potassium citrate preparations (mainly magistral preparations or preparations with immediate release) are commonly used for preventing urinary lithiases that occur at physiological pH and/or during urinary acidosis and/or during hypocitraturia and/or during hypercalciuria and/or during hyperoxaluria. Patients presenting such calculi are strongly recommended to continue the alkaline treatment for life.

Urocit-K is a commercial sustained-release pharmaceutical composition comprising potassium citrate and a microcrystalline wax, and is in the form of tablets. The quoted sustained action of Urocit-K has been observed in vitro. Urocit-K displays low gastric tolerance. Moreover, this formulation is not suitable for children owing to the size of the tablets.

However, according to Harvey (*J. Clin. Pharmacol.* 1989; 29: 338-341), Urocit-K has a dissolution profile in vivo close to that observed with an immediate dissolution profile. In fact, Harvey showed that (immediate-release) liquid preparations and Urocit-K, sustained-release preparation, have the same physiological effect on alkalization of the urine. Therefore Urocit-K behaves in vivo as an immediate-release pharmaceutical composition.

Moreover, one drawback of ingesting citrate salt is its low gastric tolerance, which limits the amounts that can be absorbed in a single administration. Thus, the liquid formulations with immediate action are to be taken with meals, dividing the administrations over the course of the day. Moreover, the citrate salts have a particularly unpleasant taste that is disliked by patients and quite particularly children.

Studies (Hess B. Néphrolithiase [Nephrolithiasis]. Forum Med Suisse. 2001; 45: 1119-1127) have shown that treating patients with citrate salts in immediate-release preparations had to be stopped early for 36% and 48% of patients treated with citrates because of the bad taste of the medicaments and/or side-effects, mainly gastrointestinal (bloating, eructation, diarrhoea), most often during the first six months. In comparison, the treatments were only interrupted in 12 and 31% of cases receiving placebo.

Thus, the existing medicaments comprising citrate salt as active ingredient present problems in respect of administration and/or side-effects, greatly restricting their use. There is still a need for a medicament suitable for urinary lithiases occurring at physiological pH and/or during urinary acidosis and/or during hypocitraturia and/or during hypercalciuria and/or during hyperoxaluria.

The composition according to the invention addresses these problems, and in particular it makes it possible to preserve the advantages of the citrate salts, while overcoming the drawbacks mentioned above.

The composition according to the invention is a solid pharmaceutical composition for oral use in the form of at least one tablet, said tablet consisting of a core comprising at least one Krebs cycle precursor salt as active ingredient, preferably as the only active ingredient, and a coating comprising at least one coating agent, said composition comprising from 40% to 80%, preferably from 50 to 70%, by weight of Krebs cycle precursor salt based on the total weight of the composition, said composition being able to release the Krebs cycle precursor salt in vitro, both in a dissolution medium of purified water at pH 7 and in a dissolution medium of solution buffered at pH 1.3, with a dissolution apparatus of type 2, according to the European Pharmacopoeia 2.9.3 *"Dissolution test for solid dosage forms"*, at a rate of from 2 to 15% in 15 minutes, from 15 to 25% in 30 minutes, and from 30 to 50% in one hour.

Preferably, said tablet consists of a core and a coating.

Typically and preferably, the in vitro dissolution of the composition according to the invention in a given dissolution medium, according to the conditions described above, is pH-independent. This means that, whatever the pH of the dissolution medium in a range between 1.3 and 7, the dissolution will occur similarly. In this case the applicant selected two different dissolution media, each characterized by its pH, namely pH 1.3 and pH 7, for defining this profile in a characteristic manner, advantageously according to a test that is easily reproducible in vitro.

Thus, the tablet according to the invention is coated. According to the definition in the European Pharmacopoeia (Ph. Eur.), a coated tablet is a tablet covered with one or more layers of a mixture of various substances such as natural or synthetic resins, gums, gelatin, insoluble inactive fillers, sugars, plasticizers, polyols, waxes, colourants permitted by the competent authority and, sometimes, flavourings and active substances. However, according to the invention, it is excluded that the coating comprises a Krebs cycle precursor salt.

When the coating consists of a very thin polymer film, the tablet is called film-coated (cf. Ph. Eur.).

Advantageously, the coating makes it possible both to mask the taste and to control the release kinetics of the Krebs cycle precursor salt.

The "tablet core" is, according to the invention, the whole tablet excluding the coating.

By "Krebs cycle precursor salt" is meant, according to the invention, at least one salt selected from fumarates, malates, citrates, alpha-ketoglutarate, succinyl CoA (or succinyl-coenzyme A), succinates and oxaloacetate. These salts all play a role in the Krebs cycle.

By "pharmaceutical composition" is meant, according to the invention, a composition the components of which are acceptable from a pharmaceutical standpoint. In particular, the composition consists of components that are suitable and acceptable for oral pharmaceutical administration.

By "component selected from the elements" is meant that the component is one of the elements or is a mixture of these elements.

The pharmaceutical composition according to the invention very advantageously permits continuous in vivo release in a controlled manner, for a time generally of at most four hours after administration, i.e. after a single administration. By continuous release is meant, according to the invention, a release that takes place constantly in vivo, from taking the composition up to a time of about four hours at most. Such a release is described as "sustained" because it reaches or exceeds a duration of one hour.

This controlled release observed in vitro reflects a controlled release in the organism, which can be verified by measuring the urinary pH of subjects treated with this composition, usually at regular intervals, for example every two hours.

Preferably, the pharmaceutical composition according to the invention is such that it releases in vivo practically all the Krebs cycle precursor salt (i.e. at least 95% of said salt) over a maximum time of about four hours after a single administration of the composition.

Without wishing to be bound by any hypothesis, the applicant thinks that the mechanism of action is such that, when the composition is administered orally to a subject and the Krebs cycle precursor is the citrate, the citrate is released gradually and in a controlled manner, thus being absorbed in the duodenum and the jejunum. Moreover, owing to this release, which can be described as "slow", the possibility of alkalosis of the blood is avoided.

Thus, these release kinetics advantageously make it possible to optimize the amount of Krebs cycle precursor salt administered and hence the quantity of Krebs cycle precursor salt absorbed by the organism and acting as alkalizing agent.

Consequently, the composition according to the invention is particularly suitable for alkalizing the urine and for treating acidosis occurring during certain urinary diseases, and it makes possible an anti-acidosis action that is more effective than the formulations of the prior art.

Moreover, gastric tolerance is advantageously improved relative to the formulations of the prior art, mainly owing to a gradual release of the active ingredient for a maximum time typically of from about 120 to about 240 minutes, which makes it possible to avoid an excessive burst effect in the patient's body that would be likely to cause alkalosis.

The Krebs cycle precursor salt is particularly preferably a citrate salt.

The citrate salt is preferably selected from potassium citrate, sodium citrate and magnesium citrate, and even more preferably the citrate salt is potassium citrate.

According to the invention, the composition according to the invention is able to release (or dissolve) the Krebs cycle precursor salt in vitro in a dissolution medium of purified water at pH 7 carried out with a dissolution apparatus of type 2, according to the European Pharmacopoeia (Ph. Eur.) 2.9.3 *"Dissolution test for solid dosage forms"*, at a rate of from 2 to 15% in 15 minutes, from 15 to 25% in 30 minutes, and from 30 to 50% in one hour.

This pH of 7 is a measurement that is easy to perform in the laboratory, as it is the pH of purified water. The measurement is therefore simply carried out by dissolution in purified water.

According to the invention, the composition according to the invention is able to release (or dissolve) the Krebs cycle precursor salt in vitro in a dissolution medium of solution buffered at pH 1.3 carried out with a dissolution apparatus of type 2, according to the European Pharmacopoeia (Ph. Eur.) 2.9.3 *"Dissolution test for solid dosage forms"*, at a rate of from 2 to 15% in 15 minutes, from 15 to 25% in 30 minutes, and from 30 to 50% in one hour.

This pH of 1.3 is representative of the acidic medium of the stomach.

In general, in vitro dissolution of the composition according to the invention in a given dissolution medium, according to the conditions described above, is independent of the pH. This means that, whatever the pH of the dissolution medium in a range between 1.3 and 7, dissolution takes place according to the same kinetics. In this case the applicant selected two different dissolution media, each characterized by its pH, namely pH 1.3 and pH 7, for defining this profile in a characteristic manner, according to a test that is easily reproducible in vitro.

For these measurements, one gram of pharmaceutical composition, which corresponds to a unit dose, is placed in a dissolution apparatus of the Pharmatest type, model PTW S3C, in which the temperature conditions are 37° C.±0.5° C., and the rotary speed is 100 rpm (revolutions per minute). The volume of the dissolution vessel is 1 L and the dissolution medium used is purified water at pH 7 or a solution buffered at pH 1.3.

The Krebs cycle precursor salt, and in particular the citrate salt, is analysed as is known by a person skilled in the art. For example, the potassium citrate released is analysed with a flame photometer, the analytical method having been validated according to the ICH recommendations CPMP/ICH/381/95-ICH Q2 (R1).

Thus, release of an excessive amount of Krebs cycle precursor salt is avoided since the form comes into contact with the dissolution liquid advantageously according to the invention. This makes it possible to avoid a burst effect in the patient's body, in contrast to the compositions of the prior art. Moreover, the dissolution kinetics of the Krebs cycle precursor salt are advantageously slowed at the start of dissolution, which in particular improves the gastric tolerance of the product compared with the products of the prior art.

Preferably, the Krebs cycle precursor salt is completely dissolved (degree of dissolution of 100%) in about four hours, whether the pH is 7 or 1.3.

The composition according to the invention comprises from 40% to 80%, preferably from 50 to 70%, by weight of Krebs cycle precursor salt based on the total weight of the composition. The Krebs cycle precursor salt is thus present in a dose that is physiologically effective or represents a multiple or a sub-multiple of an effective dose for a standard patient.

This represents a high level of active ingredient, by weight relative to the total weight of the composition, compared with what is known. This advantageously makes it possible to minimize the volume of the pharmaceutical composition, and therefore the volume of daily administration. As a consequence, this results in better acceptance by the patient.

This is particularly significant for taking the composition in high doses and/or for paediatric therapeutic treatments.

The coating agent is generally selected from alginates, carboxyvinyl polymers, sodium salts of carboxymethyl cellulose, cellulose derivatives including the polymers hydroxypropyl methylcellulose, hydroxypropyl ethylcellulose, hydroxypropyl cellulose, hydroxyethyl cellulose, methylcellulose, ethylcellulose, xanthan gum and polyethylene oxide, waxes such as paraffin wax, beeswax or carnauba wax, ammonium methacrylate copolymers of type A and B as described in the European Pharmacopoeia, and polyacrylates of about 30% dispersion as described in the European Pharmacopoeia. Preferably, according to the invention, the coating agent is an ethylcellulose polymer.

According to one embodiment of the invention, the coating comprises, besides a coating agent such as selected from the above list, a flavouring agent and/or a colourant.

The thickness and homogeneity of the coating is an important parameter of the invention, as it influences the diffusion of the Krebs cycle precursor through the coating and therefore the dissolution kinetics of this precursor. Selection of the nature and of the amount of the coating agent used is an important parameter of the invention.

The pharmaceutical composition according to the invention generally comprises from 0.01% to 5%, preferably from 0.01% to 2% by weight, even more preferably from 1.4 to 2.5%, of coating agent relative to the total weight of the composition.

The pharmaceutical composition according to the invention can further comprise:
  from 10% to 40%, preferably from 25% to 35% by weight, relative to the total weight of the composition, of a binder selected from microcrystalline celluloses, polyvidone, polyvinylpyrrolidone, copovidone, shellac, gelatin, polymethacrylates, synthetic resins, acrylates, maltodextrin, and starches, and preferably the binder comprises at least one microcrystalline cellulose;
  from 0.01% to 5%, preferably from 0.02% to 3% by weight, relative to the total weight of the composition, of a flow agent (or lubricant) selected from stearic acid, polyethylene glycol, magnesium stearate, calcium stearate, zinc stearate, talc, silica, hydrogenated castor oil, glyceryl behenate, and glyceryl palmitostearate, and preferably the flow agent is selected from magnesium stearate and glyceryl behenate; and/or
  any suitable pharmaceutical excipient, in a quantity used conventionally in the field in question, for example from 0.0001% to 20% of the total weight of the composition.

The pharmaceutical excipient is generally inert, i.e. inactive and non-toxic, and acceptable from a pharmaceutical standpoint. Such an excipient is most often selected from diluents, binders, disintegrants, flow agent, lubricants, colourants permitted by the competent authority, dispersants, solubilizers, stabilizers, preservatives, plasticizers and flavouring agents. Such an excipient can also be a support, for example selected from the group comprising celluloses such as hydroxymethylcellulose, carboxymethylcellulose, cyclodextrins, polysorbate 80, mannitol, gelatin, lactose, vegetable oils, animal oils, carbonates, starches and acacia.

Preferably, all the tablets have the same composition and display a similar dissolution rate, which is the dissolution rate that can characterize the pharmaceutical composition of the invention.

Moreover, the tablet core of the composition according to the invention can comprise at least one sustained-release matrix, preferably with a content comprised within a range of from 10% to 30%, even more preferably from 15% to 25%, by weight relative to the total weight of the composition. Such a sustained-release matrix is preferably selected from alginates, carboxyvinyl polymers, sodium salts of carboxymethyl cellulose, cellulose derivatives including the polymers hydroxypropyl methylcellulose, hydroxypropyl ethylcellulose, hydroxypropyl cellulose, hydroxyethyl cellulose, methylcellulose, ethylcellulose, xanthan gum and polyethylene oxide, waxes such as paraffin wax, beeswax or carnauba wax, ammonium methacrylate copolymers of type A and B as described in the European Pharmacopoeia, and polyacrylates of about 30% dispersion as described in the European Pharmacopoeia.

Such a sustained-release matrix is defined as follows.

The European Pharmacopoeia (Ph. Eur.) defines, among tablets with modified release, sustained-release tablets, delayed-release tablets and sequential-release tablets. Modified-release tablets are tablets, coated or uncoated, that are prepared with special excipients, or by particular methods, or both, with the aim of modifying the rate, the place or the moment of release of the active substance(s).

In general, sustained-release tablets are tablets permitting release of an active substance that is sustained over time and according to defined kinetics. This is preferably achieved by making a tablet core, or a plain tablet (i.e. uncoated) using a sustained-release matrix containing the active substance(s). A sustained-release matrix is generally a matrix system, most often a polymer network, whether hydrophilic or lipophilic. The diffusion of the active substance(s) within this network is generally influenced not only by the intrinsic physicochemical properties of this or these active substance(s) (such as solubility, molecular weight etc.), but also by those characterizing the matrix network (such as: hydrophilicity, degree of polymerization, gelling rate, erosion).

According to a preferred embodiment of the invention, the pharmaceutical composition is in the form of microtablets.

The European Pharmacopoeia (Ph. Eur.) defines a tablet as a solid preparation containing an administration unit of one or more active substances. Tablets are obtained by agglomerating a constant volume of particles by compression, or by some other suitable method of manufacture such as extrusion, moulding or freeze-drying (lyophilization). Tablets are intended for the oral route. Tablets are generally in the form of a right cylinder, the lower and upper faces of which can be flat or convex and the edges bevelled. The size of a tablet, or average dimension, is therefore generally the diameter of this cylinder, or an equivalent. However, if the height of the cylinder is significant, and greater than the diameter of the cylinder, the size of the tablet is the height of this cylinder.

By "microtablet" is generally meant, according to the invention, a tablet with a size comprised within a range of from 2 to 4 mm (generally with the size accurate to ±10%). Preferably, all the microtablets have the same composition and they each have a similar dissolution rate, which is the dissolution rate that can characterize the pharmaceutical composition of the invention. This dissolution rate is commonly established on the basis of one unit of the preparation or, in the context of the invention, one gram of microtablets. Owing to the small size of the microtablet, a single microtablet will not be sufficient for one administration, and several microtablets will be administered for each dose.

An advantage of the microtablet form is that patients find them easier to take, compared with taking a single tablet of larger volume. This is particularly advantageous when the patient is a child.

It is understood that, according to the invention, the patient will be able to ingest several microtablets at each administration, depending on the therapeutic dose that is suitable for him (the daily dose divided by the number of administrations per day). Thus, one administration of the medicament corresponds to several microtablets, i.e. a set of microtablets. The invention therefore also aims to cover a set of microtablets, corresponding to a therapeutic administration. A person skilled in the art is able to evaluate the number of microtablets corresponding to a therapeutic dose, as a function of the needs of the person, their age, their weight, as a function of the quantity of citrate salt per microtablet, as well as the number of administrations per day.

The microtablets according to the invention are coated, which makes it possible to mask the taste.

The tablets according to the invention are particularly suitable for treating urinary lithiases occurring at a physiological pH and/or during urinary acidosis and/or during hypocitraturia and/or during hypercalciuria and/or during hyperoxaluria, owing to their optimum release profile.

The composition according to the present invention can be used in mammals, more precisely in humans, and quite particularly in children.

The method of manufacture of the pharmaceutical composition according to the invention generally comprises the three successive steps described below.

The first step is a step of mixing the active ingredient, preferably the single active ingredient, with the other ingredients constituting the core of the pharmaceutical composition according to the invention. Mixing is carried out for example in a gravity-fed mixer of the Stuart STR4 type, but can be carried out in any other type of industrial mixer.

The second step is a step of tablet manufacture, from the mixture originating from the first step, generally carried out by a first operation of direct compression in a rotary press, for example for manufacturing microtablets of size 2 mm (of the PR12 type) using six supports each having a head with six 2-mm punches. This second step then comprises a second operation of dedusting of the tablets produced during the first operation.

The third step is a step of coating, with the coating agent, of the tablets originating from the second step. The coating agent is generally applied in the form of solution or suspension under conditions that promote evaporation of the solvent.

According to one embodiment of the invention, the composition comprises from 55% to 70% potassium citrate, from 20 to 40% microcrystalline cellulose, from 0.02% to 3% magnesium stearate, from 0.01% to 1% glyceryl behenate and from 1 to 3% ethylcellulose polymer, relative to the total weight of the composition.

The invention also relates to a composition according to the invention for use as a medicament.

The invention also relates to a composition according to the invention for use as a medicament in the treatment and/or prevention of urinary lithiases occurring at a physiological pH and/or during urinary acidosis and/or during hypocitraturia and/or during hypercalciuria and/or during hyperoxaluria.

The invention is illustrated in the attached FIG. 1, which shows the dissolution profile as the dissolution rate T (percentage of active ingredient–potassium citrate) as a function of time t (min) for four different compositions/conditions identified by A1 and A2 (composition according to the invention and pH of 7 and 1.3 respectively) and B1 and B2 (compositions according to the prior art, Urocit-K, and pH of 7 and 1.3 respectively).

FIG. 1 is referred to in the example below, which illustrates the invention without however limiting it.

EXAMPLE

A batch of microtablets of 2 mm size (average diameter) is produced according to the method described above, namely a step of mixing the powders, followed by a compression step, then a coating step. This batch is batch A, and consists of 200 g of microtablets. These microtablets have the following composition:

Potassium citrate (active ingredient, source Dr Paul Lohmann): 66.9%

Microcrystalline cellulose (binder, Ceolus® KG-802 from the company Asahi): 19.7%

Microcrystalline cellulose (binder, Ceolus® UF-711 from the company Asahi): 9.8%

Magnesium stearate (flow agent): 2.0%

Glyceryl behenate (lubricant, commercial reference Compritol® ATO 888 from the company GATTEFOSSE): 0.01%;

Ethyl cellulose polymer (coating agent, commercial reference Ethocel® 20 standard premium from the company Dow): 1.66%.

These microtablets are very well accepted and tolerated by patients. Moreover, they have no taste and are easy to swallow.

FIG. 1 shows the in vitro dissolution profile of one gram of these microtablets in water, under the conditions described below, over a period of 2 hours. Microtablets A were put in a Pharmatest dissolution apparatus, model PTW S3C, in which the temperature conditions are 37° C.±0.5° C., and the rotary speed is 100 rpm. Depending on the dissolution medium, two different curves were obtained, A1 and A2 respectively, for a solution of purified water at pH 7 and for a solution buffered at pH 1.3. Curves A1 and A2 are approximately identical, above all for a period of less than 1 h or even thirty minutes.

As shown in FIG. 1, the microtablets of batch A are able to release the citrate salt in vitro in a dissolution medium of purified water at pH 7, as well as in a solution buffered at pH 1.3, at a rate respectively of 4.5 and 3.7% in 15 minutes, of 20.6 and 18.6% in 30 minutes, and of 48.6 and 44.0% in one hour.

Generic tablets of Urocit-K were purchased commercially in the form of a box of 90 tablets with the reference "Potassium citrate (1080 mg) Tabs MFG RISING—Generic for Urocit-k 1080 mg (10 meq) Tablets RX 1505494-03363", sold by WALGREENS, Indianapolis, USA. The experiment was repeated on these tablets. Two different curves were obtained, B1 and B2 respectively, for a solution of purified water at pH 7 and for a solution buffered at pH 1.3. Curves B1 and B2 are approximately identical, above all for a period of less than 1 h or even thirty minutes. Curves B1 and B2 intersect curves A1 and A2 for a period between 1 h and 1.5 h.

As shown in FIG. 1, the Urocit-K tablets A are able to release the citrate salt in vitro in a dissolution medium of purified water at pH 7, as well as in a solution buffered at pH 1.3, at a rate respectively of 37.0 and 42.1% in 30 minutes, and of 50.5 and 55.1% in one hour.

FIG. 1 shows that the dissolution curves according to the invention (A1 and A2) and according to the prior art (B1 and B2) are very different, in particular at the start of dissolution, where the values of the slopes are very different. This demonstrates a gradual and much slower release of the active ingredient, namely the citrate salt according to the invention, avoiding a burst effect in the organism, which would be likely to cause alkalosis. Moreover, this difference can certainly partly explain the considerable improvement in gastric tolerance compared with Urocit-K.

The invention claimed is:

1. A solid pharmaceutical composition for oral use in the form of at least one tablet, said tablet consisting of:
   a core comprising potassium citrate as active ingredient, and from 10% to 40% by weight, relative to the total weight of the composition, of a binder selected from the group consisting of microcrystalline celluloses, polyvidone, polyvinylpyrrolidone, copovidone, shellac, gelatin, polymethacrylates, synthetic resins, acrylates, maltodextrin, and starches; and
   a coating comprising at least one coating agent selected from the group consisting of alginates, carboxyvinyl polymers, sodium salts of carboxymethyl cellulose, cellulose derivatives selected from the polymers consisting of hydroxypropyl methylcellulose, hydroxypropyl ethylcellulose, hydroxypropyl cellulose, hydroxyethyl cellulose, methylcellulose, and ethylcellulose, xanthan gum, polyethylene oxide, ammonium methacrylate copolymers of type A and B as described in the European Pharmacopoeia, and polyacrylates of about 30% dispersion as described in the European Pharmacopoeia,
   said tablet core comprising from 40% to 80% by weight of the potassium citrate based on the total weight of the composition,
   said composition being able to release the potassium citrate in vitro, both in a dissolution medium of purified water at pH 7 and in a dissolution medium of solution buffered at pH 1.3, with a dissolution apparatus of type 2, according to the European Pharmacopoeia 2.9.3 *"Dissolution test for solid dosage forms"*, at a rate of from 2 to 15% in 15 minutes, from 15 to 25% in 30 minutes, and from 30 to 50% in one hour, wherein gradual release of the potassium citrate occurs for a maximum time of 120 to 240 minutes wherein potassium citrate is the sole active ingredient in the composition.

2. The composition according to claim 1, wherein the coating further comprises from 0.01% to 5% of coating agent relative to the total weight of the composition.

3. The composition according to claim 1, wherein the tablet core further comprises from 0.01% to 5%, relative to the total weight of the composition, of a flow agent selected from the group consisting of stearic acid, polyethylene glycol, magnesium stearate, calcium stearate, zinc stearate, talc, silica, hydrogenated castor oil, glyceryl behenate, and glyceryl palmitostearate.

4. The composition according to claim 1, wherein the tablet core further comprises at least one sustained-release matrix, with a content comprised within a range of from 10% to 30% by weight relative to the total weight of the composition.

5. The composition according to claim 1, wherein the composition is in the form of microtablets having a size comprised within the range of from 2 to 4 mm.

6. The composition according to claim 1, wherein the tablet core comprises from 55% to 70% potassium citrate, from 20 to 40% microcrystalline cellulose, from 0.02% to 3% magnesium stearate, from 0.01% to 1% glyceryl behenate and from 1 to 3% ethylcellulose polymer, relative to the total weight of the composition.

7. A solid pharmaceutical composition for oral use in the form of at least one tablet, said tablet consisting of:
   a core comprising at least one Krebs cycle precursor salt as active ingredient, and from 10% to 40% by weight, relative to the total weight of the composition, of a binder selected from the group consisting of microcrystalline celluloses, polyvidone, polyvinylpyrrolidone, copovidone, shellac, gelatin, polymethacrylates, synthetic resins, acrylates, maltodextrin, and starches; and
   a coating comprising at least one coating agent,
   said composition comprising from 40% to 80% by weight of a Krebs cycle precursor salt based on the total weight of the composition,
   said composition being able to release the Krebs cycle precursor salt in vitro, both in a dissolution medium of purified water at pH 7 and in a dissolution medium of solution buffered at pH 1.3, with a dissolution apparatus of type 2, according to the European Pharmacopoeia 2.9.3 *"Dissolution test for solid dosage forms"*, at a rate of from 2 to 15% in 15 minutes, from 15 to 25% in 30 minutes, and from 30 to 50% in one hour wherein said at least one Krebs cycle precursor salt is the sole active ingredient in the composition.

8. The composition according to claim 7, wherein the at least one coating agent is selected from the group consisting of alginates, carboxyvinyl polymers, sodium salts of carboxymethyl cellulose, cellulose derivatives selected from the polymers consisting of hydroxypropyl methylcellulose, hydroxypropyl ethylcellulose, hydroxypropyl cellulose, hydroxyethyl cellulose, methylcellulose, and ethylcellulose, xanthan gum, polyethylene oxide, ammonium methacrylate copolymers of type A and B as described in the European Pharmacopoeia, and polyacrylates of about 30% dispersion as described in the European Pharmacopoeia.

9. A method of delivering a citrate salt in a controlled manner, comprising administering a composition according to claim 1 to a subject in need thereof.

10. A method for the treatment and/or prevention of urinary lithiases occurring at a physiological pH and/or during urinary acidosis and/or during hypocitraturia and/or during hypercalciuria and/or during hyperoxaluria, comprising administering to a patient in need thereof an effective amount of the composition according to claim 1.

* * * * *